| United States Patent [19] | [11] Patent Number: 4,810,825 |
|---|---|
| Matsushita et al. | [45] Date of Patent: Mar. 7, 1989 |

[54] METHOD OF REDUCING NITRILE INTO A CORRESPONDING ALCOHOL

[75] Inventors: Hajime Matsushita, Yokohama; Makoto Shibagaki, Kawasaki; Kyoko Takahashi, Tokyo, all of Japan

[73] Assignee: Japan Tobacco, Inc., Tokyo, Japan

[21] Appl. No.: 129,662

[22] Filed: Dec. 7, 1987

[30] Foreign Application Priority Data

Dec. 11, 1986 [JP] Japan .................................. 61-293469

[51] Int. Cl.$^4$ ............................................. C07C 29/00
[52] U.S. Cl. .................................................... 568/840
[58] Field of Search ..................................... 568/840 R

[56] References Cited

U.S. PATENT DOCUMENTS

| 3,056,817 | 10/1962 | Werber | 568/840 R |
| 4,144,401 | 3/1979 | Wall | 568/840 R |
| 4,626,604 | 12/1986 | Hiles et al. | 568/840 R |

FOREIGN PATENT DOCUMENTS

| 0215563 | 8/1986 | European Pat. Off. | 568/840 R |
| 1237089 | 3/1963 | Fed. Rep. of Germany | 568/840 R |

OTHER PUBLICATIONS

Houben-Weyl, "Methoden der Organischen Chemie", 4th edition, vol. VI/1b, part III, 1984, Georg Theime Verlag, Stuttgart, New York, p. 361.

*Primary Examiner*—Alan L. Rotman
*Assistant Examiner*—Robert C. Whittenbaugh
*Attorney, Agent, or Firm*—Nixon & Vanderhye

[57] ABSTRACT

A method of reducing a nitrile into a corresponding alcohol is disclosed. The nitrile is caused to react with an alcohol by using a zirconium hydrous oxide as a catalyst. The zirconium hydrous oxide is obtained by partially dehydrating zirconium hydroxide. The nitrile can be reduced to the corresponding alcohol in a one-step reaction.

5 Claims, No Drawings

METHOD OF REDUCING NITRILE INTO A CORRESPONDING ALCOHOL

BACKGROUND OF THE INVENTION

1. Field of the Invention

The present invention relates to a method of reducing a nitrile into a corresponding alcohol and, more particularly, to a new and useful method of causing a nitrile to react with an alcohol in the presence of a catalyst, to obtain a desired alcohol.

2. Description of the Prior Art

Various conventional methods of reducing nitriles are known to those skilled in the art. A first conventional method is reduction by a hydride compound such as lithium aluminium hydride or aluminium hydride. A second conventional method s reduction of nitrile with an alkali metal such as lithium, sodium, or calcium in aqueous ammonia or an amine solvent. A third conventional method is electrolytic reduction, and a fourth is reduction by catalytic hydrogenation, using a heterogeneous catalyst.

When nitriles are reduced according to the above methods, the primary products produced are generally amines or, in special cases, aldehydes. The amine is converted into an alcohol via diazotation, while the aldehyde can be reduced and converted into an alcohol by sodium borohydride or the like, ("Shin Jikken Kagaku Kouza" Vols. 14 and 15, Maruzen).

Meerwein-Ponndorf-Verley reduction is a known reducing method which uses an inexpensive alcohol such as isopropanol as a hydride source. However, the purpose of this method is known to derive an alcohol from an aldehyde or ketone, not to reduce a nitrile (A. L. Wilds, Org. React., 2, 178, 1944).

The above conventional methods present the following problems.

According to the first method, expensive hydride compounds such as lithium aluminium hydride and aluminium hydride must be used. These hydride compounds are highly reactive with water, and thus care must be taken in their storing and handling. In addition, the reactivity is too strong, and produce highly flammable hydrogen gas.

According to the second method, an active metal, i.e., an alkali metal (e.g., lithium or sodium) or an alkaline earth metal (e.g., calcium) is used. These active metals, however react vigorously with water, giving rise to spontaneous ignition, and so are difficult to handle. Further, in order to obtain the reaction product, the non-reacted metal must be deactivated with water, and extraction carried out using an organic solvent, thus necessitating cumbersome and time-consuming operations.

According to the third method, an apparatus specifically designed for electrolysis must be employed. This method is therefore not economical.

According to the fourth method, i.e, reduction over heterogeneous catalytic hydrogenation, care must be taken, as hydrogen gas is used.

According to the above conventional methods, desired alcohols cannot be primarily obtained. As described above, the primary products in the above methods are mainly amines or, in special cases, aldehydes. In order to derive alcohols from amines or aldehydes, additional steps is required. In general, a reaction for diazotating amines to obtain alcohols produces a low yield. In particular, when a primary amine is used, the reaction involves isomerization, and a primary alcohol cannot be obtained generally. Use of sodium borohydride, to reduce an aldehyde into an alcohol, is expensive and care must be taken in its handling.

SUMMARY OF THE INVENTION

It is an object of the present invention to provide a simple, safe, and inexpensive method by means of which a nitrile can be reduced into an alcohol in one step and with a high yield.

According to the present invention, there is provided a reducing method for causing a nitrile to react with an alcohol by using a zirconium hydrous oxide as a catalyst and reducing the nitrile into a corresponding alcohol.

The zirconium hydrous oxide used as the catalyst in the present invention is a rigid, solid material which is physically and chemically stable, and is obtained by partially dehydrating zirconium hydroxide. Zirconium hydrous oxide is insoluble in alcohols or other organic solvents, is chemically and thermally stable, and inexpensive to produce. It is highly active as a reducing catalyst for accelerating a reaction using an alcohol as a hydrogen source. Thus, zirconium hydrous oxide is a highly suitable catalyst for the reaction of the present invention.

DETAILED DESCRIPTION OF THE PREFERRED EMBODIMENT

The most important characteristic feature of the present invention is use of zirconium hydrous oxide as a catalyst. Zirconium hydrous oxide is obtained when zirconium hydroxide is heat-treated under conditions wherein it is not converted into a perfect oxide and the heat-treated zirconium hydroxide is partially dehydrated. When zirconium hydroxide is heated at a temperature of 500° C. or more at atmospheric pressure, it is completely dehydrated whereby zirconia ($ZrO_2$) is obtained. However, when zirconium hydroxide is heated at about 300° C., it is partially dehydrated and becomes to stable. After approximately one hour of heat treatment, the zirconium hydroxide is reduced in weight by around 17%. Thereafter, further weight loss rarely occurs.

Zirconium hydrous oxide is a rigid, white, solid material. Since it is also amorphous, it cannot be analyzed by X-ray diffraction, and thus its detailed chemical structure is not known. However, the chemical structure of zirconium hydrous oxide can be assumed on the basis of the fact that zirconium hydroxide is partially dehydrated. Zirconium hydrous oxide has a Zr—O—Zr bond formed by dehydration-condensation, with hydroxyl groups directly bonded to Zr atoms also remaining. As described above, zirconium hydrous oxide is insoluble in water and organic solvents and is stable as a heterogeneous catalyst. The zirconium hydrous oxide does not cause elution and swelling, and has excellent resistance to heat and solvents. In addition, as a result of the above properties, it can be used repeatedly. Moreover, the zirconium hydrous oxide has been confirmed to have low surface acidity and good ion exchangeability with various ions.

The zirconium hydrous oxide can be easily obtained, at low cost, as follows:

Zirconium hydroxide is obtained from zirconium minerals, which are present in a relatively large quantities, and is heat-treated and partially dehydrated so as to produce zirconium hydrous oxide. When zirconium hydrous oxide is used as a catalyst, it can be pulverized into grains having a desired size or may be carried on a suitable carrier such as alumina, active charcoal, silica gel, silica-alumina, or zeolite.

The method of the present invention can be embodied as a gaseous phase reaction, using a reaction tube filled with the catalyst. The reaction tube is heated to a temperature suitable for the reduction reaction, to occur, and a nitrile dissolved in alcohol is continuously supplied to the reaction tube, by use of a suitable inert carrier gas, and bought into contact with the catalyst bed. When the reaction temperature is less than 200° C., this results in an increase in the amount of an ester which occurs as byproducts, with a consequent decrease in the yield of the desired alcohol. When the reaction temperature above 340° C., the dehydration of the produced alcohol is promoted, and thus the desired alcohol cannot be recovered. Therefore, the reaction temperature must fall within the range of 200° to 340° C., and more preferably 280° to 320° C.

The product is recovered as follows:

The outlet of the reaction tube is cooled with water, ice, or any other suitable refrigerant, thereby condensing effluent gas containing products and nonreacted materials. The desired product can be isolated from the condensed mixture by fractional distillation. The molar ratio of the nitrile to the alcohol is selected to be within the range of 1/20 to 1/130.

The preparation of the catalyst used in the present invention, as well as the reduction method of the invention will now be described in greater detail, by way of examples.

EXAMPLE 1

(Preparation of Catalyst)

In this example, 200 g of zirconium oxychloride (octahydrate) were dissolved in 10 l of deionized water, and 1N sodium hydroxide aqueous solution was slowly added under stirring to attain pH 6.8, thereby precipitating a hydrated gel of zirconium hydroxide. The hydrated gel was filtered and the resultant gel was washed with fresh deionized water. Washing was repeated until no chloride ions were detected in the filtered water. The resultant hydrated gel was cut into pieces by a knife, the pieces placed on a glass plate, and dried at room temperature, whereby 90 g of zirconium hydroxide were obtained.

The resultant zirconium hydroxide (24 to 60 mesh) was heated at 300° C. for 3 hours at atmospheric pressure and partialy dehydrated, whereby a zirconium hydrous oxide was obtained. A weight loss of about 17% occurred as a result of the heat treatment.

EXAMPLE 2

(Reduction of Nitrile)

In this example, 2.0 g of the zirconium hydrous oxide prepared in Example 1 were used as the catalyst, being placed in a reaction tube made of a heat-resistant glass and having an inner diameter of 4 mm and a length of 500 mm. The reaction tube was placed in an electric furnace and the temperature therein was set at 300° C.

A solution composed of a mixture (mixing molar ratio: 1:65) of isobutyronitrile and 2-propanol was prepared as a source material for the synthesis reaction, and was supplied to the reaction tube by means of a microfeeder. The carrier gas, in this case, was nitrogen gas at a flow rate of 1 ml/sec. The solution was supplied to the carrier gas at a rate of 10 ml/hour.

The source material was supplied, together with the carrier gas, into the reaction tube, where it came into contact with the catalyst layer therein. After the reaction, the resultant gas was guided outside the reaction tube and was condensed by cooling. The condensate was analyzed by gas chromatography, to identify the product. The conversion rate and selectivity rate of the reaction were calculated.

The conversion rate represents the ratio of the amount of source material lost in the reaction to the total amount of source material supplied therefor, and the selectivity rate represents the ratio of the amount of source material converted into a desired product to the amount of source material lost in the reaction.

Subsequently, reduction reactions took place, following the same procedures as described above, except that n-capronitrile, benzonitrile, isocapronitrile, n-valeronitrile, and pivalonitrile were sequentially used in place of isobutyronitrile as the source material. Results in the steady state are summarized in Table 1.

TABLE 1

| Nitrile | Alcohol | Product | Conversion (%) | Selectivity (%) |
| --- | --- | --- | --- | --- |
| isobutyronitrile | 2-propanol | isobutyroalcohol | 98 | 95 |
| n-capronitrile | 2-propanol | n-hexanol | 89 | 78 |
| benzonitrile | 2-propanol | benzyl alcohol | 98 | 64 |
| isocapronitrile | 2-propanol | 4-methylpentanol | 92 | 85 |
| n-valeronitrile | 2-propanol | n-pentanol | 98 | 73 |
| pivalonitrile | 2-propanol | 2,2-dimethyl-propanol | 89 | 90 |

EXAMPLE 3

(Dependency on Reducing Agent)

In this example, the dependency of the reduction reaction on the alcohols used as reducing agents in the present invention was examined. For this purpose, six alcohols were used for reducing a single type of nitrile, the nitrile, in this case, being n-valeronitrile. The alcohols used as the reducing agents were 2-propanol (mixing molar ratio: 1 (nitrile):65 (alcohol)), cyclohexanol (1:24), α-methylbenzyl alcohol (1:21), benzyl alcohol (1:46), methanol (1:130), and ethanol (1:85). The reaction apparatus and operation conditions were same as in Example 2. The results are shown in Table 2.

TABLE 2

| Nitrile | Alcohol | Product | Conversion (%) | Selectivity (%) |
| --- | --- | --- | --- | --- |
| n-valeronitrile | 2-propanol | n-pentanol | 98 | 73 |
| n-valeronitrile | cyclohexanol | n-pentanol | 71 | 76 |
| n-valeronitrile | α-methylbenzilalcohol | n-pentanol | 20 | 100 |
| n-valeronitrile | benzilalcohol | n-pentanol | 5 | 20 |
| n-valeronitrile | methanol | n-pentanol | 33 | 2 |
| n-valeronitrile | ethanol | n-pentanol | 73 | 55 |

EXAMPLE 4

(Temperature Dependency)

In this example, the dependency on the reaction temperature of the nitrile reduction reaction of the present invention was examined. For this purpose, a solution composed of a mixture (mixing molar ratio: 1:65) of n-butyronitrile and 2-propanol was used as a source material, and the reaction temperature was changed, in six steps, within the range of 200° to 340° C. The reaction apparatus and the like were the same as those used in Example 2. The results are summarized in Table 3.

TABLE 3

| Nitrile | Alcohol | Product | Reaction Temperature (°C.) | Conversion (%) | Selectivity (%) |
|---|---|---|---|---|---|
| n-valeronitrile | 2-propanol | n-pentanol | 340 | 100 | 41 |
| n-valeronitrile | 2-propanol | n-pentanol | 320 | 100 | 76 |
| n-valeronitrile | 2-propanol | n-pentanol | 300 | 98 | 73 |
| n-valeronitrile | 2-propanol | n-pentanol | 280 | 73 | 85 |
| n-valeronitrile | 2-propanol | n-pentanol | 250 | 40 | 55 |
| n-valeronitrile | 2-propanol | n-pentanol | 200 | 37 | 14 |

According to the present invention as described above in detail, an inexpensive alcohol, which acts as a reducing agent, and a catalyst which is safe and easy to handle can be used together in a one-step reaction whereby a nitrile can be reduced into an alcohol, and a high yield obtained.

What is claimed is:

1. A method of reducing a nitrile into the corresponding alcohol, which comprises reacting the nitrile with an alcohol at a reaction temperature of 200° C. to 340° in the presence of a zirconium hydrous oxide catalyst and reducing the nitrile into the corresponding alcohol in a one-step reaction.

2. A method according to claim 1, wherein the zirconium hydrous oxide is pulverized into grains having a desired size and is used without further modification.

3. A method according to claim 1, wherein the zirconium hydrous oxide catalyst is carried on a suitable carrier selected from the group consisting of alumina, active charcoal, silica gel, silica-alumina, and zeolite.

4. A method according to claim 1, wherein a reaction tube filled with the catalyst is heated to the reaction temperature, a solution composed of the nitrile and the alcohol is continuously fed into the reaction tube by means of an inert carrier gas and is brought into contact with the catalyst.

5. A method according to claim 1, wherein the reaction temperature is within a range of 280° to 320° C.

* * * * *